United States Patent [19]
Bawden

[11] Patent Number: 5,679,401
[45] Date of Patent: Oct. 21, 1997

[54] MEDICAL MARKING DEVICE AND ITS USE

[76] Inventor: Dean T. Bawden, 2400 W. 7800 South, Suite 209, West Jordan, Utah 84088

[21] Appl. No.: 567,899

[22] Filed: Dec. 6, 1995

[51] Int. Cl.$^6$ .................................................. A61C 3/00
[52] U.S. Cl. .............................. 427/2.29; 433/2; 433/25
[58] Field of Search ................... 106/19 R; 427/2.24, 427/2.29; 433/2, 25

[56] References Cited

U.S. PATENT DOCUMENTS

| | | |
|---|---|---|
| 3,068,571 | 12/1962 | Thompson . |
| 3,756,727 | 9/1973 | Gallagher ................................. 401/84 |
| 4,065,887 | 1/1978 | Shrader .................................. 51/358 |
| 4,202,337 | 5/1980 | Hren et al. ........................ 128/303.14 |
| 4,500,221 | 2/1985 | Emerson ................................ 401/82 |
| 4,595,136 | 6/1986 | Cooper ................................... 228/57 |
| 4,667,412 | 5/1987 | Carlson ................................. 33/138 |
| 4,870,922 | 10/1989 | Robertson ............................ 118/702 |
| 5,290,253 | 3/1994 | Kira ..................................... 604/190 |
| 5,312,250 | 5/1994 | Ellman et al. .......................... 433/77 |
| 5,326,261 | 7/1994 | Rains ................................... 433/141 |

*Primary Examiner*—Diana Dudash
*Attorney, Agent, or Firm*—Thorpe, North & Western

[57] ABSTRACT

A medical marking device and method of use are disclosed. The marking device is formed at least partially of soapstone, and the method includes the use of the marking device on prosthetics disposed in or to be used in a human body. Between uses, the soapstone marking device is sterilized by placing it in an autoclave with other medical instruments. Unlike prior marking devices, the soapstone actually increases in strength as it is sterilized.

3 Claims, 1 Drawing Sheet

MEDICAL MARKING DEVICE AND ITS USE

BACKGROUND OF THE INVENTION

1. Field of the Invention

The present invention relates to a reusable medical marking device for marking metals and the like and, in particular, to a method of marking metal and other materials to be used in a human body with a medical marking device which can be sterilized without melting or otherwise deteriorating when placed in an autoclave.

2. Background Art

The use of medical marking devices to mark metal which is currently within a patient's body or which will be placed in a patient's body is well known. Of the many uses for such a marking device, the most frequent is that of orthodontic prosthetics which are used to straighten teeth. In the process of adjusting the teeth, the orthodontist must repeatedly adjust wires to pull the teeth into the desired location. This is accomplished by forming small bends in the wire. The position at which the bend is made depends on both the present and desired location of the teeth.

To ensure that the bends are made in the appropriate location, orthodontists temporarily position the wires within the patient's mouth and make marks indicating the desired location of the bends. The wire is then withdrawn so that the appropriate bends can be made. Making the bends outside of the mouth is easier for the orthodontist, and reduces the risk of accidently scratching or puncturing the cheek or gums of the patient with the wire.

Due to the difficulty of marking metal, there has been several different approaches for leaving a mark which can be readily seen by the orthodontist when the wire is removed from the mouth. The most common is the use of wax. In one common method, wax is disposed on a toothpick or similar device. The toothpick is contacted against the wire to leave a wax mark at the desired location of the bend. Such a method is often slow, as several toothpicks may be required for a wire requiring a large number of bends. Additionally, the toothpicks are generally expensive and are not convenient to hold.

An alternative to the toothpick approach is a pencil having a wax core which is used to mark the wire. While the pencil avoids the need for numerous toothpicks, it cannot be sterilized, as the heat would quickly melt the wax. Reuse of the pencil without sterilization is not acceptable due to the risk of passing diseases between patients. This is especially true in orthodontics where bleeding in the mouth can lead to the transmission of blood bourn diseases. Thus, a pencil is usually thrown away after use on a single patient. The pencil method, however, is not preferred because of the waste of materials and the expense involved. A patient may only have two or three bends which must be made in their wire, and using an entire pencil to mark the same is extremely wasteful.

Similar problems are present in other areas of medicine. Whenever a metal plate or pin is to be used in a patient, any markings that may be required must be carefully considered as unsterilized wax could contain pathogens which will jeopardize the success of the surgery or other application. However, prior to the present invention, there has not been an available method for making marks on metal and similar materials to be disposed in a patient. Of course, the type of metal being used raises concerns, a light colored metal may be easily marked with a dark colored marking, but will generally not facilitate marking with a lightly colored marking material.

When a piece of metal or other prosthetic material, such as ceramics and composites, is placed in a human body, the physician, dentist or orthodontist must be able to make accurate marks in the material to bend, shape or cut the material properly. Such may be required, for example, when placing a plate in a human body. If a bore hole must be formed in the plate, it is critical to mark the location appropriately. However, as with the orthodontic applications discussed above, the prior art mechanisms for marking the material has generally not met with success.

Thus, there is a need for a medical marking device which can be used to mark metal and which can readily be sterilized to prevent the transmission of disease when used on several different patients. Such a device should be inexpensive and easy to use. The device should also enable the marking of different colored metals and of other rigid materials such as ceramics and composites.

SUMMARY OF THE INVENTION

Thus, it is an object of the present invention to provide a medical marking device which can be used to mark metal and other similar materials and which can be sterilized.

It is another object of the present invention to provide such a medical marking device which is inexpensive and easy to use.

It is another object of the present invention to provide such a medical marking device which decreases waste generated by enabling the repeated use thereof on numerous different patients.

The above and other objects of the invention are realized in specific illustrated embodiments of a Medical Marking Device including a sterilizable marking material formed to leave a mark on metal, ceramics and other rigid materials when the sterilizable marking material is forcefully contacted against the metal.

In accordance with one aspect of the invention, the marking material is steatite, i.e. compact aggregates of basic magnesium silicate minerals (talc). The hard steatite is commonly referred to as soapstone. The soapstone marks orthodontics and other metal prosthetics so that the bends can be made, holes drilled, or whatever other modifications need be made. Because the soapstone can withstand temperatures well in excess of 212° F., it can be sterilized in an autoclave. Thus, the marking device can be used on numerous different patients without the risk of transmitting disease.

Soapstone is advantageous for several reasons. First, soapstone is widely available around that world and need not be transported long distances. Second, soapstone can come in a variety of colors, ranging from a pale, whitish color, as seen in common talc, to a dark green. The different colors which are available facilitate the marking of different colors or metals, ceramics, etc. If a light material need be marked, a dark piece of soapstone can be used. Conversely, a white piece of soapstone can be used to mark dark metals.

Because soapstone is generally inexpensive, the overall cost to the orthodontist, dentist or physician is significantly decreased. Autoclaving the soapstone consumes very little if any additional energy and the soapstone marking device will last for dozens of patients. Additionally, soapstone is interesting in that it is strengthened by exposure to high temperatures. More than a century ago, soapstone was used to form the orifice in gas burners. Thus, not only will the soapstone not melt when autoclaved, as would the wax marking devices of the prior art, the soapstone will actually be strengthened by the sterilization procedure.

In accordance with another aspect of the invention, a handle is provided for holding the marking material. As with the marking material, the handle should be able to be sterilized in an autoclave or some other manner. The handle will typically be formed of stainless steel. Because many materials may become slick when contacted by bodily fluids, the handle may be provided with a roughened surface, such as knurled rings, to prevent the medical marking device from slipping from the hand of the orthodontist, dentist, or physician using the device.

In accordance with yet another aspect of the invention, the handle is formed integrally from the marking material to form a unitary piece of material. Thus, when soapstone is used, the medical marking device is formed entirely from a piece of soapstone. Preferably, the piece of soapstone will be formed in shape of a pencil. A single piece of soapstone formed as a pencil may be used on dozens and possibly even hundreds of patients. Between each use, the soapstone is merely placed in the autoclave with the other orthodontic instruments and heated to a sufficient temperature to kill pathogens contained thereon. The soapstone may also be sharpened to provide a fine point for marking if desired. However, because the soapstone is hard and is strengthened by the heat of the autoclave, the fine point will last considerably longer than such a point formed in wax.

In accordance with yet another object of the invention, when the soapstone is formed to serve as its own handle, a textured surfaces is provided along at least a part of the handle to prevent slippage. Those familiar with soapstone will appreciate that steatite obtained this name due to its soap-like feel. If a textured surface is not provided, the soapstone can become slippery when contacted by body fluids.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Figure 1:
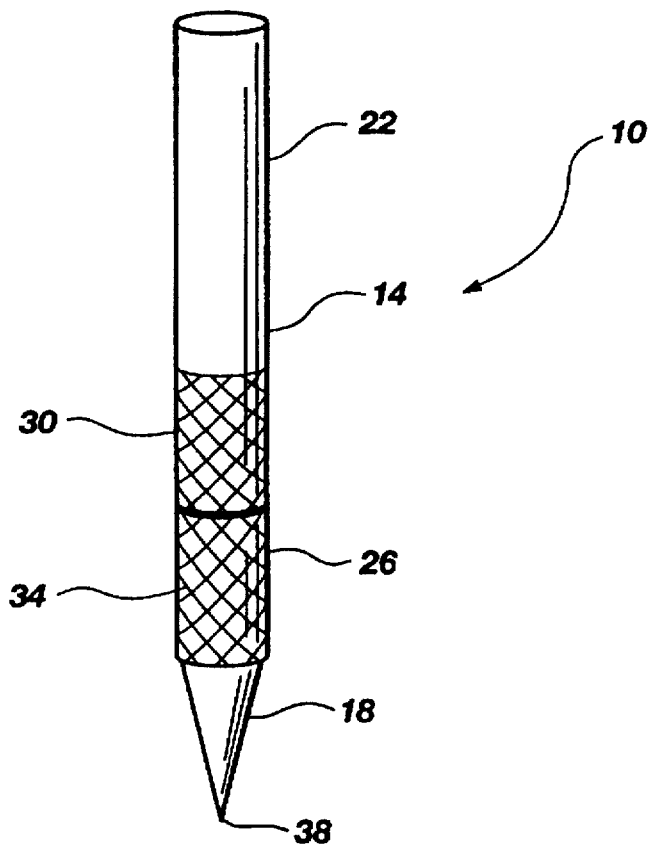
FIG. 1 shows a perspective view of a medical marking device made in accordance with the principles of the present invention.

Referring to FIG. 1, there is shown a perspective view of a medical marking device, generally indicated at 10. The device includes an elongate handle 14 which is configured to receive a piece of soapstone 18. The handle 14 will typically be made out of a hollow, cylindrical durable material which can withstand the heat of an autoclave. Thus, stainless steal is a desired material.

The handle 14 includes a first, rearward portion 22 into which the soapstone 18 can extend, and a second, forward portion 26 which rotates relative to the first rearward portion. By rotating the second, forward portion 26, the soapstone 18 can be locked into place relative to the handle 14 to prevent the soapstone from moving when pressure is applied thereto. Both portions, 22 and 26 of the handle 14 will typically have knurled surfaces, such as is shown at 30 and 34, or some other texturing to promote traction of the respective portions. Such is important because the orthodontist, dentist or physician using the marking device 10 will usually be wearing gloves. When the gloves or handle 14 are contacted by body fluids, a nontextured handle would tend to slide relative to the gloves when force is applied.

The soapstone 18 will typically be honed to a point 38 to facilitate the placement of fine markings on braces or other prosthetics. This is typically accomplished by a file or some other mechanism. Because soapstone is fairly hard, however, the point 38 will last a considerable amount of time before resharpening is required. As the soapstone 18 is subjected to the heat of an autoclave, the strength of the soapstone will actually increase.

After use the marking device 10 can be placed into an autoclave with the other instruments used by the orthodontist, physician, etc. The autoclave is then turned on and given time to sterilize the instruments and the marking device. Because autoclaves are used by virtually all dentists, orthodontists and physicians, the medical marking device 10 of the present invention will not increase costs. To the contrary, a marking device 10 which may cost little more than conventional wax marking pencils may be used to mark one hundred patients or more. Thus, considerable cost savings is achieved, not to mention the substantial decrease in waste generated by use of the reusable marking device 10. This is especially true in that the wax pencils which are thrown away may still carry pathogens, while the autoclaved soapstone 18 will not.

Figure 2:
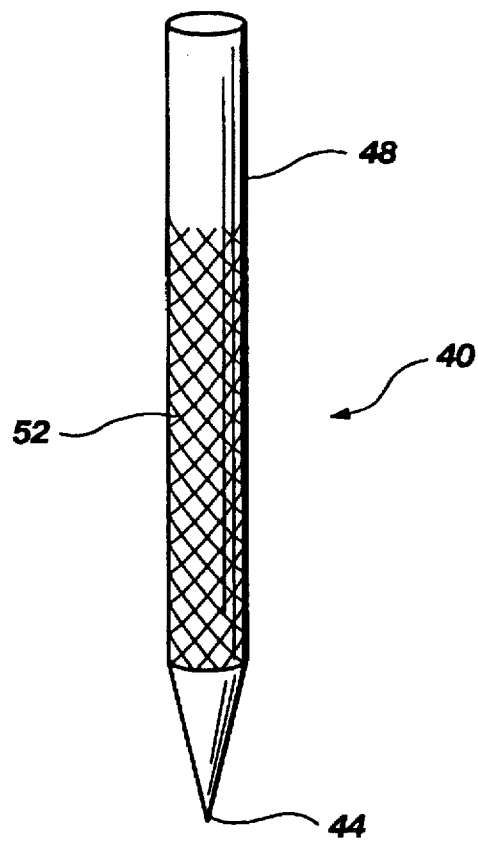
FIG. 2 shows an alternate embodiment of a medical marking device in accordance with the teachings of the present invention.

Referring now to FIG. 2, where is shown a perspective view of an alternate embodiment of the present invention. To further reduce costs, the handle 14 (FIG. 1) can be omitted and the marking device, generally indicated at 40, can be formed solely from the soapstone. Because soapstone is durable, the material is typically formed in the shape of a pencil with a pointed end 44 for marking, and an elongate cylindrical portion 48 for grasping. While the soapstone will break under extreme pressure, it is hard enough to withstand all contemplated uses thereof.

Because soapstone can be slippery when wet, a part of the elongate cylindrical portion 48 can be textured, i.e. knurled, etc., to provide improved grip. The textured surface is easily formed by forming small cuts about the exterior of the soapstone.

Thus there is disclosed a medical marking device and method which permits the user to mark a rigid prosthetic such as orthodontic braces, crowns, and metal plates, etc. used in a human body while maintaining an aseptic environment. The method includes, for example, selecting a soapstone marking device and forcefully contacting the soapstone marking device against the piece of metal to be used in the medical procedure to leave a mark on the piece of metal. Of course materials such as ceramics and composites may also be marked with the soapstone. The soapstone should preferably be sterilized between each use on different patients.

By providing a marking device having a soapstone marking agent disposed therein which is capable of withstanding temperatures sufficient to sterilize the marking agent and marking device without melting and improved method is achieved. Subjecting the marking device and marking agent to temperatures sufficient to sterilize the marking device and marking agent, a marking device is achieved which can be used to mark metal and other materials to be disposed within the body of a patient, sterilized and then reused on a second patient.

Those skilled in the art will appreciate that numerous modifications can be made to the present invention without departing from the scope or spirit thereof. Such modifications are intended to be covered by the appended claims.

What is claimed is:

1. A method for positioning braces in the mouth of a patient as part of an aseptic medical procedure, the method comprising:

a) selecting a sterile soapstone marking device;

b) selecting a dental brace material to be disposed within a patient during a medical procedure;

c) identifying a location on the material for bending or deforming while positioning the brace material within the mouth of the patient;

d) forcefully contacting the sterile soapstone marking device against the brace material at the identified location to be used in the medical procedure to leave a mark on said material; and e) bending or deforming the material at the location identified by the soapstone mark in accordance with the medical procedure.

2. The method to be used in a medical procedure of claim 1, wherein the method comprises marking a piece of metal to be disposed in a patient's mouth.

3. A method for using a medical marking device for marking brace material as defined in claim 1, comprising the more specific steps of:

a) selecting a medical marking device having a soapstone marking agent disposed therein which is capable of withstanding temperatures sufficient to sterilize the soapstone marking agent and marking device without melting;

b) subjecting the marking device and soapstone marking agent to temperatures sufficient to sterilize the marking device and soapstone marking agent; and c) using the marking device to mark metal to be disposed within the body of a patient.

* * * * *